(12) United States Patent
El-Massri

(10) Patent No.: US 12,139,739 B2
(45) Date of Patent: Nov. 12, 2024

(54) BIOGAS PRODUCTION FROM EXCREMENT

(71) Applicant: Lakeside Power and Methane, LLC, Charlotte, NC (US)

(72) Inventor: Mahmoud A. El-Massri, Charlotte, NC (US)

(73) Assignee: Lakeside Power and Methane, LLC, Charlotte, NC (US)

( * ) Notice: Subject to any disclaimer, the term of this patent is extended or adjusted under 35 U.S.C. 154(b) by 898 days.

(21) Appl. No.: 17/192,404

(22) Filed: Mar. 4, 2021

(65) Prior Publication Data
US 2021/0198700 A1    Jul. 1, 2021

Related U.S. Application Data

(62) Division of application No. 16/101,880, filed on Aug. 13, 2018, now Pat. No. 10,947,565.
(Continued)

(51) Int. Cl.
*C12P 5/02* (2006.01)
*A01K 67/033* (2006.01)
(Continued)

(52) U.S. Cl.
CPC ............ *C12P 5/023* (2013.01); *A01K 67/033* (2013.01); *A23K 10/26* (2016.05); *A23K 50/90* (2016.05);
(Continued)

(58) Field of Classification Search
None
See application file for complete search history.

(56) References Cited

U.S. PATENT DOCUMENTS

2002/0177219 A1    11/2002    Oliver
2003/0143728 A1     7/2003    Oliver
(Continued)

FOREIGN PATENT DOCUMENTS

WO         2013100840 A1    7/2013

OTHER PUBLICATIONS

Newton, GL; et al; "Dried Hermetia illucens Larvae Meal as a Supplement for Swine" Journal of Animal Science, 44, 395-400, 1977 (Year: 1977).*
Devic, Emilie Danielle Paule; "Assessing Insect-Based Products as Feed Ingredients for Aquaculture" Doctoral Thesis, University of Stirling, Jun. 2016 (Year: 2016).*
(Continued)

Primary Examiner — David W Berke-Schlessel
(74) Attorney, Agent, or Firm — Hammer & Associates, P.C.

(57) ABSTRACT

A method for producing biogas includes: anaerobically digesting excrement with an additive, the additive including a pre-pupal stage of an insect from the scientific classification superfamily of Stratiomyoidea; and collecting the biogas. A method for producing an additive for anaerobic digestion of excrement includes: hatching eggs of an insect from the scientific classification superfamily of Stratiomyoidea in excrement; growing insect larvae by feeding with additional excrement; harvesting pre-pupal insect larvae; and grinding the pre-pupal larvae. An apparatus for producing an additive for anaerobic digestion of excrement includes: a tray having pivot along one lateral side and an upwardly sloping wall terminating with a lip along a lateral side opposite the pivot; a flume adjacent the lip; and a conveyor adjacent the pivot.

10 Claims, 5 Drawing Sheets

Related U.S. Application Data

(60) Provisional application No. 62/567,390, filed on Oct. 3, 2017, provisional application No. 62/559,777, filed on Sep. 18, 2017, provisional application No. 62/545,064, filed on Aug. 14, 2017.

(51) Int. Cl.
| | |
|---|---|
| *A23K 10/26* | (2016.01) |
| *A23K 50/90* | (2016.01) |
| *C02F 3/28* | (2023.01) |
| *C02F 3/34* | (2023.01) |
| *C02F 11/04* | (2006.01) |
| *C02F 103/20* | (2006.01) |

(52) U.S. Cl.
CPC .............. *C02F 3/2893* (2013.01); *C02F 3/34* (2013.01); *C02F 11/04* (2013.01); *A01K 2227/108* (2013.01); *A01K 2227/706* (2013.01); *C02F 2103/20* (2013.01); *C02F 2305/06* (2013.01)

(56) References Cited

U.S. PATENT DOCUMENTS

| | | |
|---|---|---|
| 2012/0187041 A1 | 7/2012 | Popa et al. |
| 2015/0296760 A1 | 10/2015 | Perednia |

OTHER PUBLICATIONS

H.H. Park, "Black Soldier Fly Larvae Manual," Student Showcase, 14 ed., http://scholarworks.umass.edu.sustainableumass_studentshowcase/14 (Amherst, MA), (p. 1-13).

C.M. Williams, "Technology Report: Black Soldier Fly (SF)," Cost and Returns Analysis of Manure Management Systems Evaluated in 2005 under the North Carolina Attorney General Agreements with Smithfield Foods, Premium Standard Farm, and Front Line Farmers, NC State University (Raleigh, NC).

R.G.S. Nogueira et al., "Laboratory Evaluation of Co-Digesting Beef Manure and Waste Kitchen Oil," Presentation at the 2016 ASABE Annual International Meeting, Orlando, FL, Jul. 17-20, 2016, ASABE (St. Joseph, MI).

K. Beyer, "Anaerobic Digestion for FOG for Optimal Methane Production," San Diego State University (California), (p. 1-15).

\* cited by examiner

BIOGAS PRODUCTION FROM EXCREMENT

RELATED APPLICATIONS

This application claims the benefit of U.S. Provisional Patent Application Nos. 62/545,064 filed Aug. 14, 2017; 62/559,777 filed Sep. 18, 2017; and 62/567,390 filed Oct. 3, 2017, each is incorporated herein by reference; and U.S. Utility patent application Ser. No. 16/101,880 filed Aug. 13, 2018, now U.S. Utility Pat. No. 10,947,565, incorporated herein by reference.

FIELD OF THE INVENTION

The inventions disclosed herein are directed to the production of biogas from excrement, particularly livestock generated excrement, using an anaerobic digestion process.

BACKGROUND OF THE INVENTION

Excrement can be converted to biogas. Biogas is a gaseous fuel produced by fermentation of organic matter and generally contains methane and carbon dioxide, among other by-products of the fermentation process. The more biogas that can be economically generated from excrement, the more economical the excrement disposal process.

Large amounts of excrement are generated in the production of farm animals (or domestic animals, or livestock). For example, swine (or hog) production generates large amounts of excrement. Excrement must be disposed of in a safe and environmentally friendly manner.

One such disposal process may be the anaerobic digestion of the excrement in which biogas, containing methane, is produced. Methane is a commodity fuel with economic value. The proceeds from the sale of the methane can be used to reduce the cost of the disposal.

Accordingly, there is a need for the economic production of methane by anaerobic digestion from excrement.

SUMMARY OF THE INVENTION

A method for producing biogas includes: anaerobically digesting excrement with an additive, the additive including a pre-pupal stage of an insect from the scientific classification superfamily of Stratiomyoidea; and collecting the biogas. A method for producing an additive for anaerobic digestion of excrement includes: hatching eggs of an insect from the scientific classification superfamily of Stratiomyoidea in excrement; growing insect larvae by feeding with additional excrement; harvesting pre-pupal insect larvae; and grinding the pre-pupal larvae. An apparatus for producing an additive for anaerobic digestion of excrement includes: a tray having pivot along one lateral side and an upwardly sloping wall terminating with a lip along a lateral side opposite the pivot; a flume adjacent the lip; and a conveyor adjacent the pivot.

DESCRIPTION OF THE DRAWINGS

For the purpose of illustrating the invention, there is shown in the drawings a form that is presently preferred; it being understood, however, that this invention is not limited to the precise arrangements and instrumentalities shown.

DESCRIPTION OF THE INVENTION

In general, one invention is directed to a method for producing biogas by the steps of: anaerobically digesting (or anaerobic co-digestion) excrement with an additive; and collecting the biogas. The additive may include a pre-pupal stage of an insect from the scientific classification superfamily of Stratiomyoidea.

Biogas, as used herein, refers to a gaseous fuel produced by anaerobic digestion of organic matter and generally contains methane and carbon dioxide, among other by-products of the fermentation process. See: *Wikipedia, Biogas*, incorporated herein by reference.

Anaerobic digestion, as used herein, refers to processes where biodegradable materials are broken down, in the absence of oxygen, to produce, among other things, biogas. See: *Wikipedia, Anaerobic digestion*, incorporated herein by reference.

Excrement, as used herein, refers any excrement from any source, for example, animal or livestock (e.g., pig, cow, goat, sheep, chicken, turkey), and human. See: *Wikipedia, Feces*, and *Wikipedia, Livestock*, both incorporated herein by reference.

The additive is used to facilitate biogas production. The additive includes a pre-pupal (larva) stage of an insect from the scientific classification superfamily of Stratiomyoidea. The insect may be of the family of Stratiomyidae. The insect may be of the subfamily Hermetiinae. The insect may be of the genus *Hermetia*. In one embodiment, the insect may be *Hermetia illucens* (Black Soldier Fly or BSF larvae or BSFL). See *Wikipedia, Hermetia illucens*, and *Wikipedia, Holometabolism*, both incorporated herein by reference. The additive may be ground or pureed. The additive may further include frass. The frass may be sourced from the insect's excrement generated during the insect's larvae growth. The additive, when frass is included, may have an insect:frass ratio (by weight) of 1:0-3.0. In another embodiment, this ratio may be 1:0.5-2.0. In yet, another embodiment, this ratio may be 1:1.0-2.0. And, in another embodiment, this ratio may be 1:1.6. Production of the additive is discussed below.

Collection of the biogas from the digestion process may be performed in any conventional manner. The collected biogas may be purified to methane, to enhance value, in any conventional manner.

Figure 1:
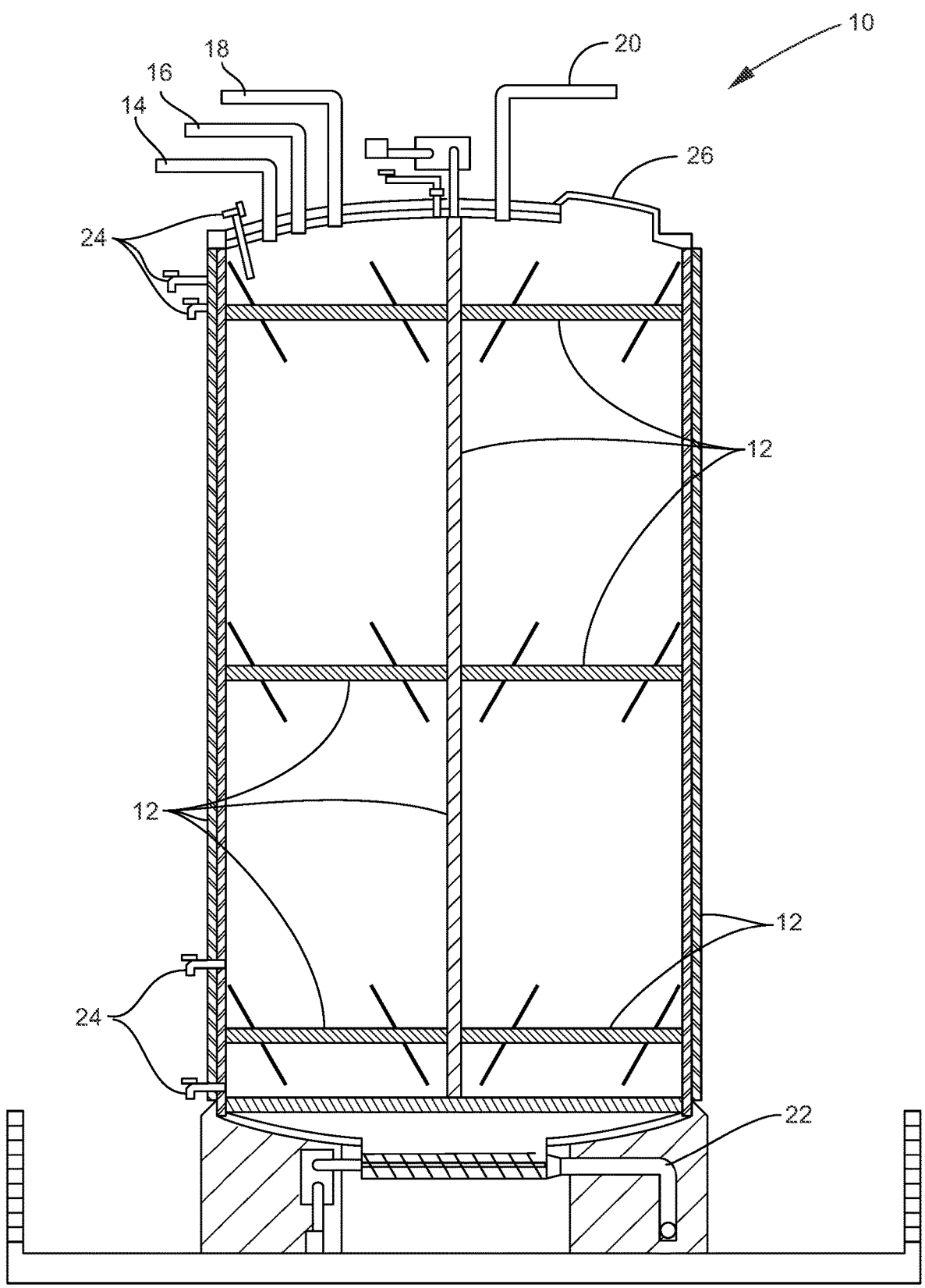
FIG. 1 is a schematic illustration of an embodiment of a digestion tank.

Generally, digestion may be conducted in a closed tank 10 with agitation 12, see FIG. 1. Tank 10 may include, for example: various inlets for charging excrement 14, additive 16, and water 18; various outlets for discharge of biogas 20 and sludge 22, sampling ports 24, and access ports 26. The charge (or biomass) is maintained, during digestion, at any temperature that facilitates digestion, for example 39±2° C. The tank may be charged and maintained during digestion, with excrement diluted to, in one embodiment, less than 15% water, in another embodiment in a range of 5-15% water, in another embodiment in a range of 12-14% water, in another 13.7% water, and all subsets thereof. During digestion, the biomass is reloaded, see FIGS. 4 (volume) and 5 (weight), at a rate of 1-7% by volume of the initial mass. In one embodiment, the reload may be in the range of 2-6%, and in another embodiment, in the range of 4-6%, and another, 6%. The reloaded material includes excrement (E) and additive (A) in ratios from 1-2:1-2 (E:A).

Figure 4:
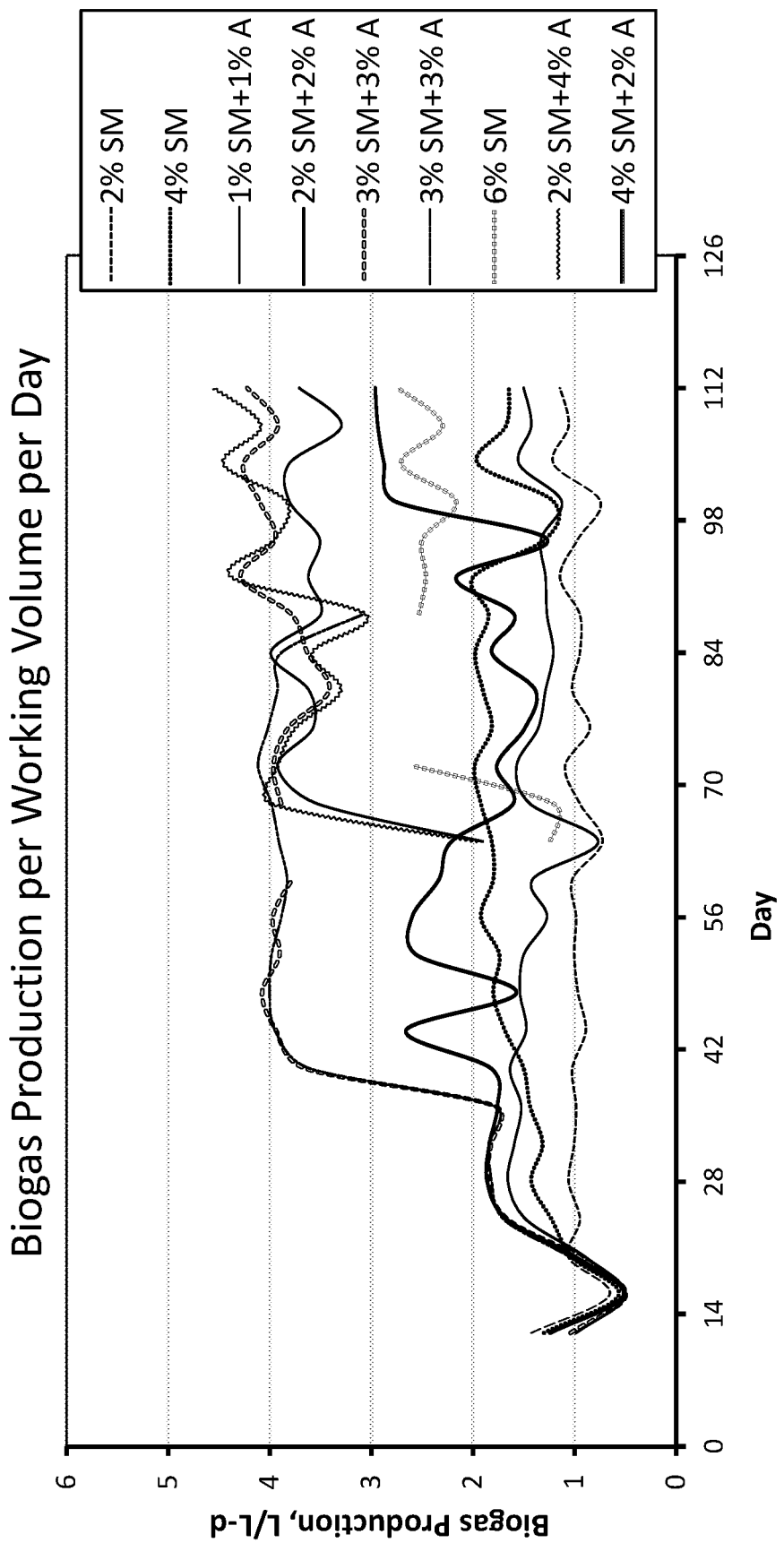
FIG. 4 is a graph illustrating biogas production per day based on volumetric loading rate during co-digestion of swine manure (SM) and additive (A) at various loading rates and mixing ratios.
Figure 5:
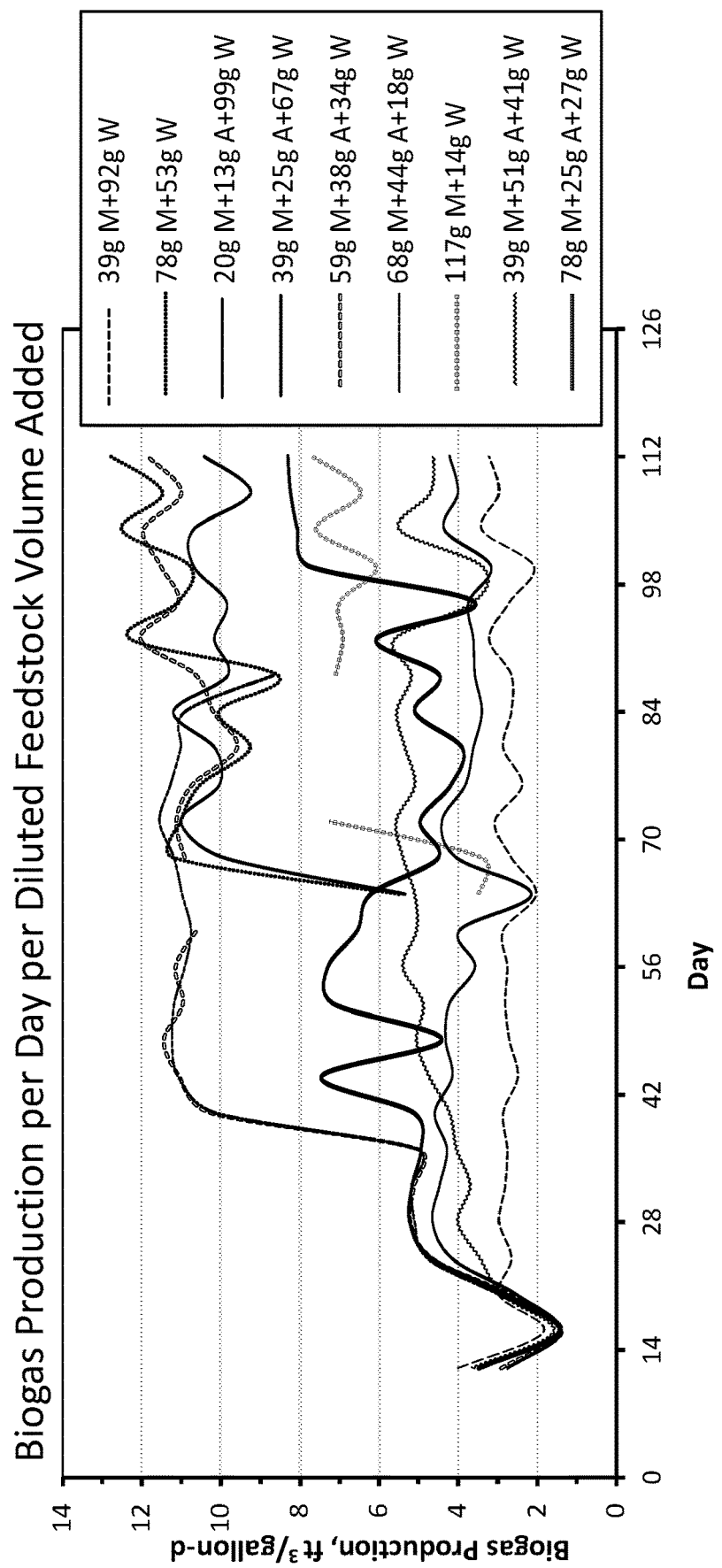
FIG. 5 is a graph illustrating biogas production per day based on diluted feedstock loading rate during co-digestion of swine manure (M) and additive (A) at various loading rates and mixing ratios.

Generally, in one embodiment, biogas production, see FIGS. 4 and 5, may be greater than 1 L/Ld per working volume of the digester. In another embodiment, biogas production may be greater than 2 L/Ld. In yet another embodiment, biogas production may be greater than 3 L/Ld. In still another embodiment, biogas production may be in a range of 1-6 L/Ld.

The additive may be produced by the method of: hatching eggs of the insect (discussed above) from the scientific classification superfamily of Stratiomyoidea in excrement; growing larvae of the insect by feeding with additional excrement; harvesting pre-pupal larvae of the insect; and particle size reduction, (e.g., grinding) the pre-pupal larvae. Additionally, grinding may include pureeing the pre-pupal larvae. The pre-pupal larvae may also include frass. Any frass not used in the additive may be collected and used as, for example, fertilizer.

Figure 2A:
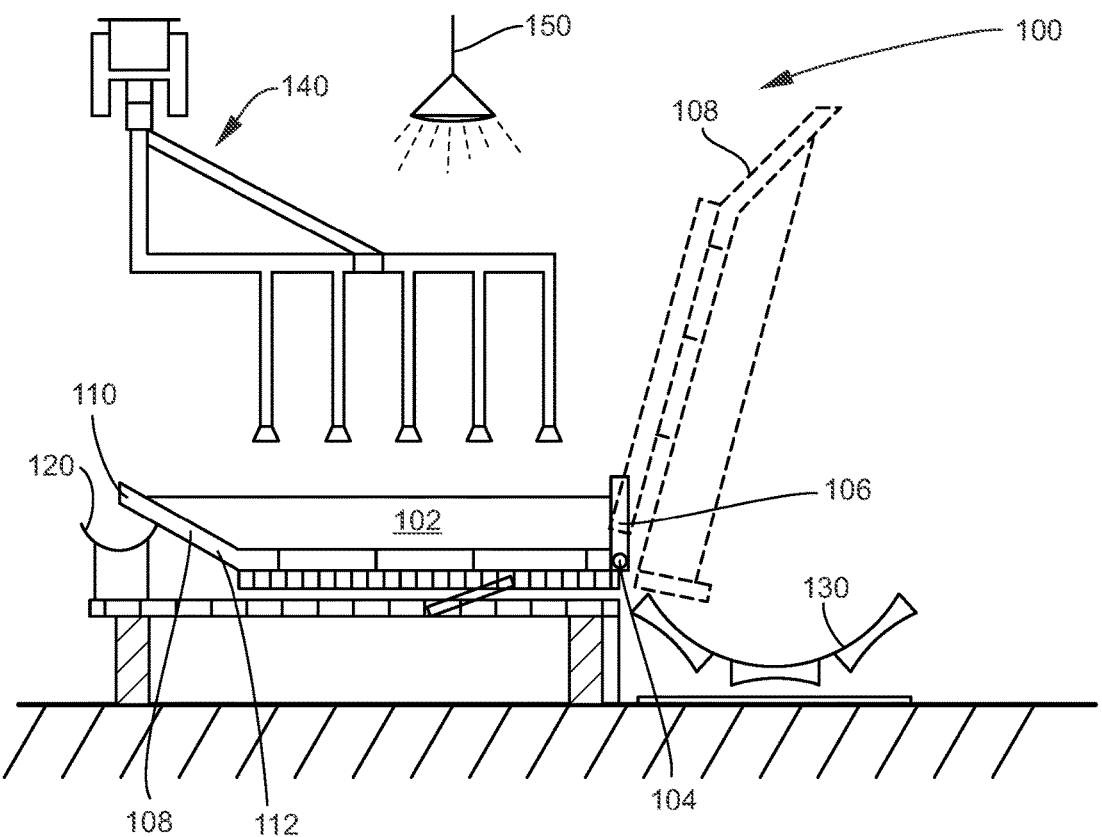
FIGS. 2A, 2B, and 2C are schematic illustrations of embodiments of an apparatus for producing additive for the production of biogas from excrement.
Figure 2B:
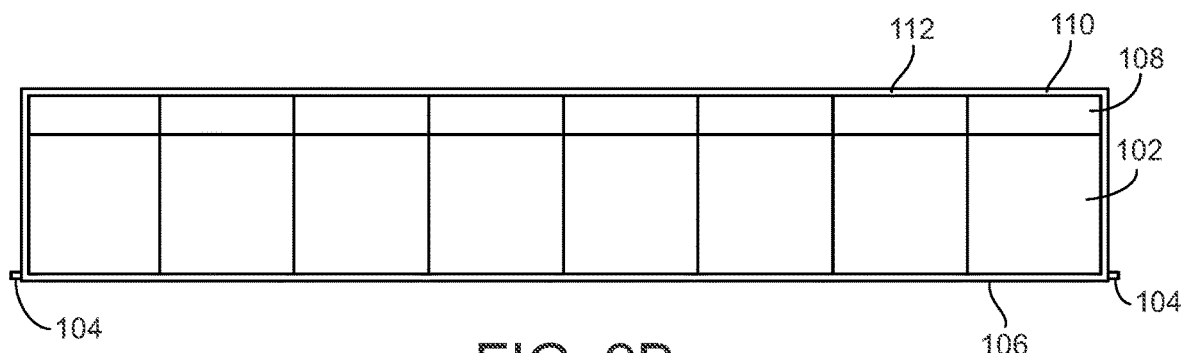
Figure 2C:
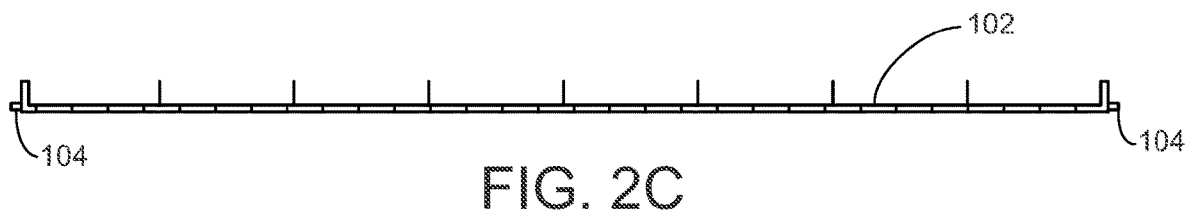

The additive may be producing in an apparatus 100, see FIGS. 2A, 2B, and 2C, including: a tray 102; a flume 120; and a conveyor 130.

Tray 102 may have a pivot 104 along one lateral side 106 and an upwardly sloping wall 108 terminating with a lip 110 along a lateral side 112 opposite the pivot 104. Tray 102 may be compartmentalized. The other walls of the tray 102 may be generally vertical (it is believed that escaping larvae will not or cannot scale the vertical walls and therefore exit via the sloped wall). The tray 102 may be movable between a horizontal position (shown in solid lines) and a generally vertical position (shown in phantom).

The flume 120 may be used to capture pre-pupal larvae exiting the tray 102 via the sloped wall 108. Flume 120 may be positioned adjacent to and below lip 110. Flume 120 may have a stream of water running therethrough to flush the captured larvae away for particle size reduction (e.g., grinding, pureeing, and/or homogenizing).

Conveyor 130 is used for removal of frass from the trays 102. Conveyor 130 is positioned adjacent to and below the pivoted side 106 of tray 102.

Additionally, apparatus 100 may include an excrement feeding system 140 for distribution of excrement during the growth of the larvae and grow lamps 150.

In use, the tray is filled with excrement, eggs from the insect are placed in the excrement, larvae hatched from the eggs grow in the excrement, excrement is added during growth (larvae may consume up to seven times their weight per day in excrement during larvae growth), the pre-pupal stage larvae exit the tray via the sloped wall and are captured in the flume, and frass from the growing larvae is dumped onto the conveyor.

The invention may be further illustrated with reference to the following examples.

EXAMPLES

Figure 3:
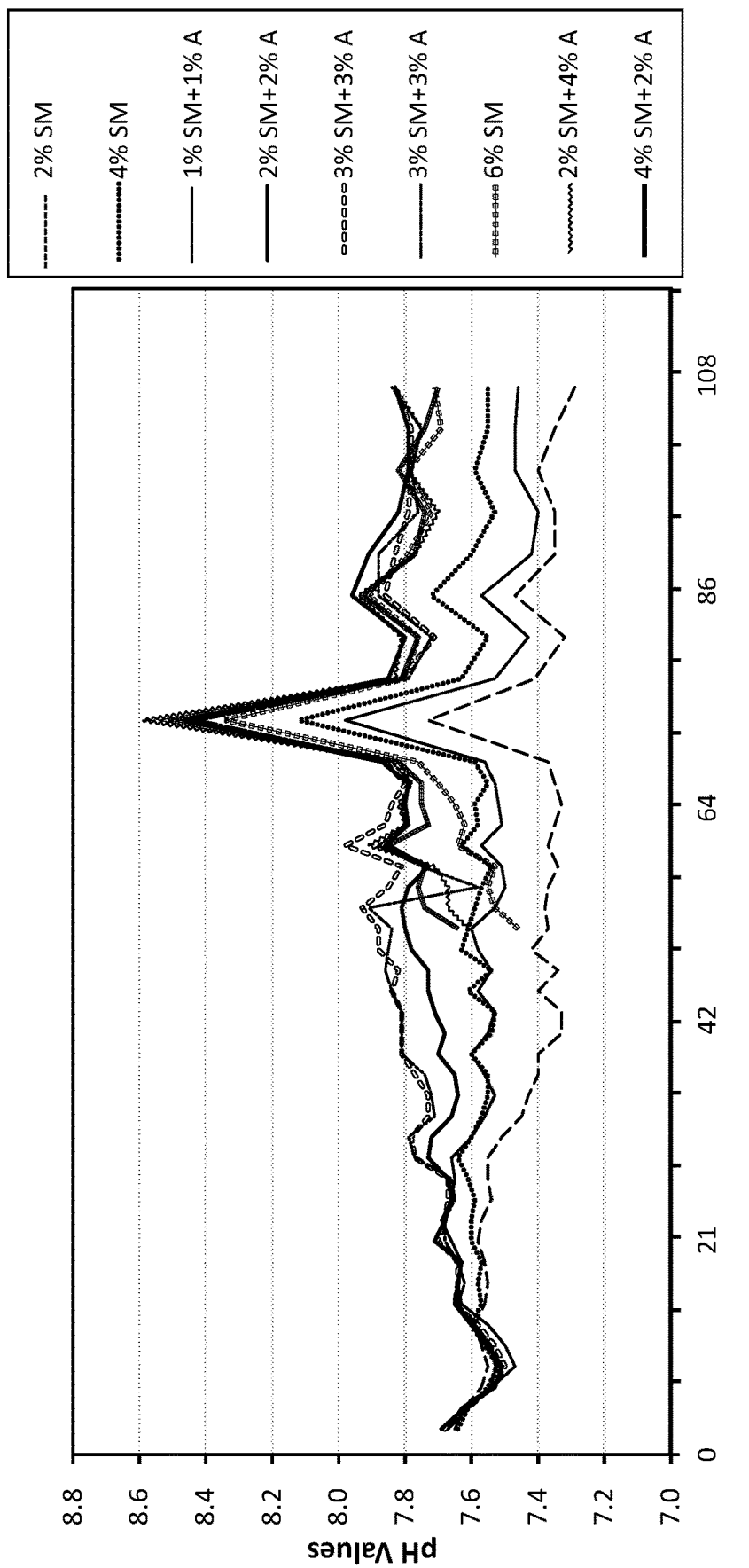
FIG. 3 is a graph illustrating the pH variation per days during co-digestion of swine manure (SM) and additive (A) at various loading rates and mixing ratios.

In the following bench-scale examples, various mixtures of swine manure (SM) and additive (A; BSFL) are co-digested diluted to about 13.7%, with semi-continuous loading (loading every two days), in glass jar digesters (1.893 L with a 1.375 L working volume) with a 21 day hydraulic retention time (HRT) at a temperature of 392° C. and with mixing (swirling digester twice a day) to characterize biogas production at various loading rates (additions of volatile solids (VS or SM) and mixing ratios (SM:A). The moisture content of the swine manure averaged 83.6% and the moisture content of the additive averaged 75.7%. FIG. 3 illustrates the pH variation per days during co-digestion of swine manure (SM) and additive (A) at various loading rates and mixing ratios. FIG. 4 illustrates biogas production per day based on volumetric loading rate during co-digestion of swine manure (SM) and additive (A) at various loading rates and mixing ratios. FIG. 5 illustrates biogas production per day based on diluted feedstock loading rate during co-digestion of swine manure (M), additive (A), and water (W) at various loading rates and mixing ratios. In FIGS. 4 and 5, methane concentration was in the range of 73-79%.

The present invention may be embodied in other forms without departing from the spirit and the essential attributes thereof, and, accordingly, reference should be made to the appended claims, rather than to the foregoing specification, as indicating the scope of the invention.

I claim:

1. A composition comprising:
   a pre-pupal stage of an insect from the scientific classification superfamily of Stratiomyoidea, wherein the pre-pupal stage of the insect is subject to a mechanical particle size reduction process prior to anaerobic production of the biogas from excrement, wherein the mechanical particle size reduction process includes grinding, pureeing, and/or homogenizing,
   frass from the insect; and
   animal excrement.

2. The composition of claim 1 wherein the insect is from the scientific classification family of Stratiomyidae.

3. The composition of claim 2 wherein the scientific classification subfamily is Hermetiinae.

4. The composition of claim 3 wherein the scientific classification species is *Hermetia illucens*.

5. The composition of claim 1 wherein the excrement is swine excrement.

6. The composition of claim 1 wherein the additive further comprises frass from the insect.

7. The composition of claim 1 wherein the biogas is methane.

8. A composition comprising:
   a pre-pupal stage of an insect from the scientific classification species is *Hermetia illucens*, wherein the pre-pupal stage of the insect is subject to a mechanical particle size reduction process prior to anaerobic production of the biogas from excrement, wherein the mechanical particle size reduction process includes grinding, pureeing, and/or homogenizing, the mechanical particle size reduction process includes grinding, pureeing, and/or homogenizing,
   animal excrement; and
   frass from the insect.

9. The composition of claim 8 wherein the biogas is methane.

10. The composition of claim 8 wherein the animal excrement is swine excrement.

* * * * *